United States Patent [19]

Sarstedt

[11] 4,396,024

[45] Aug. 2, 1983

[54] DEVICE FOR THE EXTRACTION OF CAPILLARY BLOOD

[76] Inventor: Walter Sarstedt, 5223 Nümbrecht, Rommelsdorf, Fed. Rep. of Germany

[21] Appl. No.: 90,750

[22] Filed: Nov. 2, 1979

[30] Foreign Application Priority Data

Nov. 9, 1978 [DE] Fed. Rep. of Germany ....... 2848535
Feb. 17, 1979 [DE] Fed. Rep. of Germany ....... 2906209

[51] Int. Cl.³ ............................................. A61B 5/14
[52] U.S. Cl. ................................. 128/763; 73/864.02; 73/864.72; 141/31; 422/100
[58] Field of Search ........................ 128/763, 760, 766; 73/425.4 R, 864.02; 422/100; 141/31

[56] References Cited

U.S. PATENT DOCUMENTS

| 2,237,213 | 4/1941 | Braun | 73/864.02 |
|---|---|---|---|
| 2,667,075 | 1/1954 | Blum et al. | 73/425.4 |
| 2,685,800 | 8/1954 | Natelson | 73/425.4 |
| 2,737,812 | 3/1956 | Haak | 422/100 |
| 3,141,336 | 7/1964 | Oates | 73/425.4 |
| 3,203,251 | 8/1965 | Robinson | 422/100 |
| 3,603,156 | 9/1971 | Konkol | 73/425.4 |
| 3,604,267 | 9/1971 | Johns | 422/100 |
| 3,632,119 | 12/1969 | Carpenter | 422/100 |
| 3,676,076 | 7/1972 | Grady | 73/864.02 |
| 3,739,821 | 6/1973 | Watkin et al. | 73/425.4 |
| 3,741,732 | 6/1973 | Stanfield | 73/864.02 |
| 3,864,979 | 2/1975 | Ayres | 73/864.02 |
| 3,901,085 | 8/1975 | Fauve | 73/864.02 |
| 3,952,599 | 4/1976 | Ayres | 73/864.02 |
| 4,003,262 | 1/1977 | Gerarde et al. | 128/763 |
| 4,024,857 | 5/1977 | Blecher et al. | 73/425.4 |
| 4,124,044 | 11/1978 | Nugent | 73/425.4 |

FOREIGN PATENT DOCUMENTS 22025 of 1897 United Kingdom ............... 422/100

Primary Examiner—Kyle L. Howell
Assistant Examiner—John C. Hanley
Attorney, Agent, or Firm—Townsend and Townsend

[57] ABSTRACT

In a device for the extraction of capillary blood including a capillary open at both ends and being of a predetermined volume, having a capillary effect at least at the front end thereof, a holder is integrally connected to said capillary which is provided with one or more windows.

For avoiding dosage errors, a closure pin for the rear end of the capillary or in a modification a rear transverse wall having one or more air exit apertures is provided.

12 Claims, 23 Drawing Figures

DEVICE FOR THE EXTRACTION OF CAPILLARY BLOOD

This invention relates to a device for the extraction of capillary blood including a capillary open at both ends and being of a predetermined volume, which capillary has a capillary effect at least at the front end thereof.

The blood to be extracted from a patient is thus automatically drawn into the interior of the capillary as soon as the front end thereof is brought into contact with the point of extraction.

Capillaries of this type of glass are known which have the shape of an elongate thin tube of a circular-cylindrical interior. In order to be able to draw the blood by capillary action, these capillaries have a relatively small inner diameter which is not allowed to exceed a predetermined limit.

On the other hand, an increasing reduction of the inner diameter also brings about increasing difficulties in production which then also influence cost.

For a predetermined inner diameter of these conventional capillaries, their reception volume is then determined by the respective length. In the event greater volumes are to be received, the length of such a conventional capillary then becomes excessive, and there is the risk of a fracture during or after extraction of blood. In particular, such thin and long glass capillaries are not able to be conveniently and reliably manipulated.

An object of this invention is to provide a device for the extraction of capillary blood of the species referred to initially which is able to be produced without any difficulties for various volumes in a large range and which is able to be easily and reliably manipulated.

It is in particular proposed that the opening at the rear end of the capillary is only so wide that the blood drawn in does not flow out by itself in a horizontal position of the capillary. The capillary has a bore the shape of which conforms with the possibilities of production. The bore may thus for instance be cylindrical or, provided the production method permits, flare slightly from the front end rearwardly. Thereby, the overall volume is increased. If desired, the bore of the capillary may, on the other hand, also converge from the front end rearwardly. The only thing important is that the opening at the front end is so small that there a capillary suction effect occurs. On the other hand, the opening at the rear end of the capillary must be so narrow that the blood is not able to flow out by itself.

The capillary may be conveniently manipulated by the holder. As a result of the fact that this holder is provided with windows, after effected extraction of the blood sample, washing the blood out of the sample tube by means of a diluent is facilitated.

Provided the diameter at the rear end of the capillary is selected larger than at the front end, in order to be able to accommodate a larger volume for a predetermined length, at the rear end the blood will protrude in the form of a lobe. The size of this lobe varies according to composition and temperature of the blood. For greater volumes, a dosage error would thereby result which would lead to faulty measurements. In order to avoid such dosage errors, it is proposed that the rear end of the capillary is for the major part covered by a closure pin which leaves free only small air exit apertures. This closure pin is integrally carried by a guide and retaining rod insertible in axial direction into the holder. The closure pin is applied with its face to the rear opening of the capillary and the front end of the capillary is then brought in contact with the point of extraction. The blood is thus drawn in by a capillary action and passes to the rear end of the capillary and thus to the face of the closure pin. The air displaced by the blood sample from the capillary is able to escape through the free small air exit apertures. These apertures, however, are substantially smaller than the opening at the rear end of the capillary as a total closed by the closure pin. On the one hand, a result thereof is that no blood is able to flow out even in a horizontal position or a vertical position upside down of the capillary, since said air exit apertures are too narrow to permit this. On the other hand, also only extremely small liquid lobes result at these apertures when the capillary is filled. The differences in the volumes of these small lobes as a result of different properties of the blood extracted are so minor, however, that the dosage errors resulting therefrom become negligibly small. Thus, even when using such a closure pin, it is permitted to effect a substantially more exact dosage, and a high dosage accuracy may also be sustained for very small volumes of the capillary. The expelling of the blood sample drawn in a liquid is well possible. A substantial rushing of flushing, however, is achieved in that the retaining rod is arranged preferably clampingly, but axially shiftable in the holder and may then be extracted slightly from the capillary after extraction of the blood sample. To this end, conveniently a detent means is provided which permits a withdrawal of the retaining rod by a predetermined fixed degree.

The retaining rod is preferably formed as an extended handle and then when flushing out the blood sample extracted permits a convenient holding and moving of the capillary in a flushing vessel.

Preferably, the retaining rod is provided at its lower end with at least three guide vanes generally projecting radially outwardly, said vanes guiding the lower end of the retaining rod in the holder.

Preferably, it is further proposed that both ends of the capillary are exposed. Thereby, a wetting of the portions surrounding the capillary ends with blood and thus major dosage errors are avoided. Also, the front end of the capillary when being exposed, i.e. projects axially beyond the holder, is able to be cautiously wiped clean after the extraction of blood. A contamination and the dosage errors resulting therefrom are further kept low in that the front end of the capillary externally is provided with a comparatively steep taper which has as a result a large reduction of the wall thickness of the capillary in the vicinity of the opening.

The capillary and the holder are preferably made of plastic, in particular of transparent plastic, of course a satisfactory wettability of the material having to be insured. The holder conveniently comprises two diametrically opposite webs extending parallel or generally parallel to the axis of the capillary, said webs leaving between themselves two larger windows and preferably merging at the top side into a closed tube which serves to receive the closure pin or its retaining rod and on the other hand permits a convenient manipulation.

The closure pin either rests smoothly on the rear opening of the capillary, it of course leaving free apertures at its circumference, or it has a centering projection which is formed either part-spherical or pyramidal and projects into the opening of the capillary.

Preferably for a pyramidal configuration of the centering projection, it is provided for that from the roof edges of the pyramid abutment noses having radially extending abutment faces project. These abutment noses then hold the closure pin pushed into the holder with its pyramid face in a predetermined distance from the rear opening of the capillary.

Instead of a centering projection, at the free end of the closure pin there may also be a depression in the face which likewise insures a predetermined, well-defined size of the lobe of the blood sample.

In a further embodiment, the capillary is not closed at its rear end by an applied special closure pin, but by a transverse wall in which there is or are one or more small air exit apertures.

The liquid lobes forming at these small air exit apertures have such a small volume as compared with the total volume of the capillary that virtually no dosage errors result any more. These air exit apertures, however, are necessary so that when drawing in blood air compressed in the upper portion of the capillary is able to escape. The transverse wall is either formed convex, then a single air exit aperture being located in the center thereof, or in another embodiment, it is formed concave, then either one or also several air exit apertures being located at the circumference thereof which then all lead to the bore of the capillary.

The invention is explained hereinafter in embodiments by way of example in referring to the drawings. Therein:

FIGS. 3 to 5 are the same detail view, but with an applied closure pin having a pyramidal centering projection, FIG. 3 being a sectional view taken along line III—III of FIG. 4, while FIG. 4 is a sectional view taken along line IV—IV of FIG. 3 and FIG. 5 is a sectional view taken along line V—V of FIG. 3, FIG. 18b is a plan view of the transverse wall of the embodiment of FIG. 18a.

The device illustrated in FIGS. 1 to 5 includes a capillary 1 the opening 3 of which terminates in a taper toward the extreme end 2 and a holder 4 integrally connected thereto, both made of transparent plastic. The holder 4 consists of two diametrically opposite webs 5 and 6 which merge at their upper ends as viewed in FIG. 1 in a tube 7.

Figure 1:
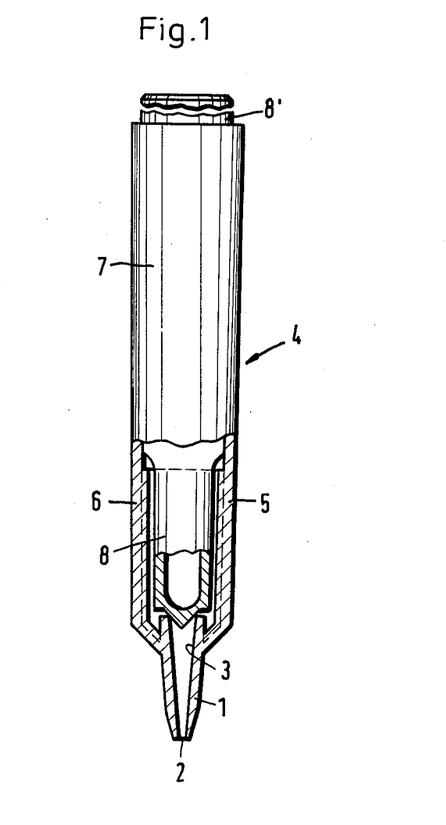
FIG. 1 is a longitudinal sectional view of a capillary according to the invention with a holder and a closure pin.
Figure 2:
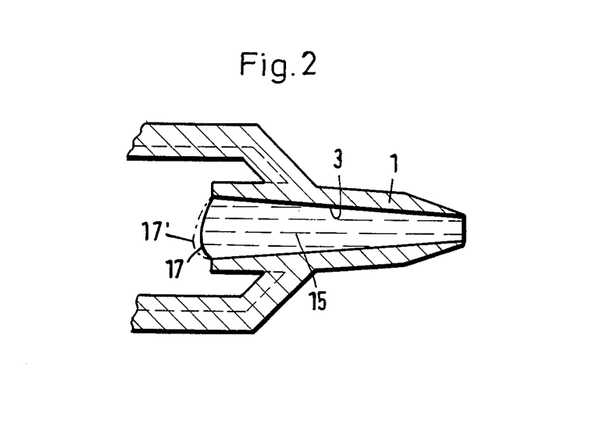
FIG. 2 is a detail view to a larger scale of the capillary with the adjacent webs, but with the closure pin omitted.
Figure 3:
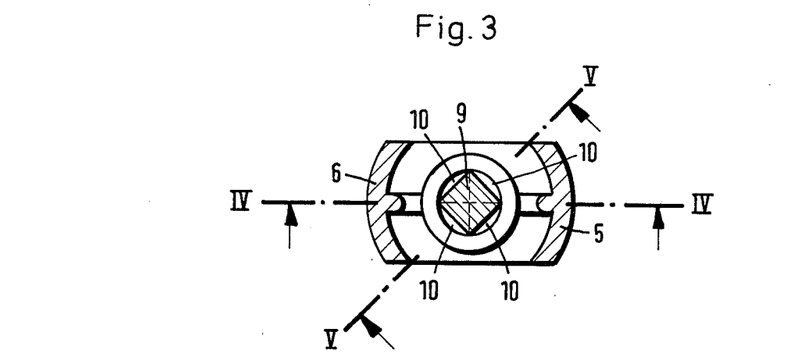
Figure 4:
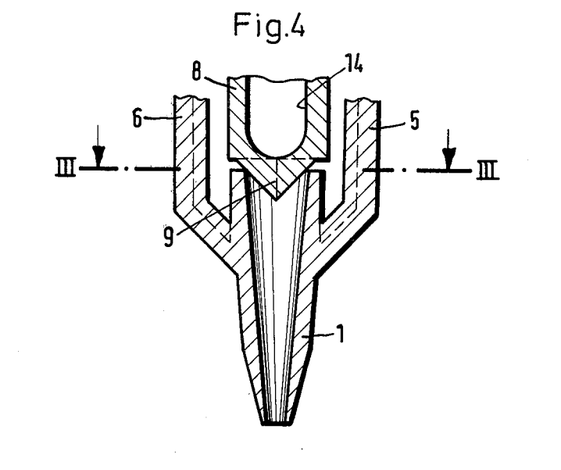

The upper or rear opening of the capillary 1 is almost completely closed by a closure pin 8, air exit apertures remaining, however. This closure pin at its rearward end or upper end as illustrated in FIG. 1 integrally merges with a retaining rod 8' which is illustrated broken in FIG. 1, but actually more or less projects over the tube 7. In a specific embodiment, this retaining rod 8' extends so far beyond the upper edge of the tube 7 that it may be used as a handle during agitating and flushing of the capillary in the sample tube illustrated in FIG. 12 which will be explained in closer detail hereinafter.

Figure 5:
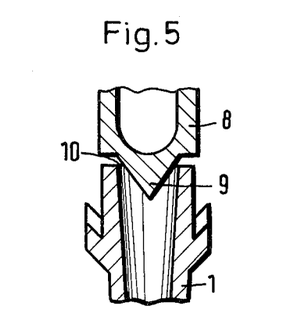

During the extraction of blood, the device is held in such a way that the end of the capillary 1 is directed inclined downwardly or even better is positioned generally horizontally with its axis. Provided then there is no closure pin 8 inserted as illustrated in FIG. 1 and the blood sample 15 has been drawn in by a capillary action at the front end of the capillary 1, the blood quantity forms at the inner flaring end of the tapered capillary a protruding lobe which slightly sags downwardly as a result of gravity. Depending on the specific properties and the temperature of the blood extracted, the lobe may also, as illustrated in phantom in FIG. 2, possess a larger volume (see 17'). Since as a result of this different size of the protruding lobe dosage errors may result, it is advisable in particular for minor overall volumes of the capillary to insert the closure pin 8 already illustrated in FIG. 1. This pin possesses, as disclosed in FIGS. 3 to 5, preferably a pyramidal centering projection 9 which rests with its edges on the inner edge or boundary wall of the upper opening of the capillary 1. However, where the surfaces of the pyramid pass the plane of the upper edge of the capillary 1, narrow, generally crescent-shaped air exit apertures 10 are formed through which upon entry of the blood drawn in as a result of the capillary action the air displaced is able to escape. In FIG. 5 representing a section taken along line V—V of FIG. 3 these air exit apertures 10 will be noted.

Figure 6:
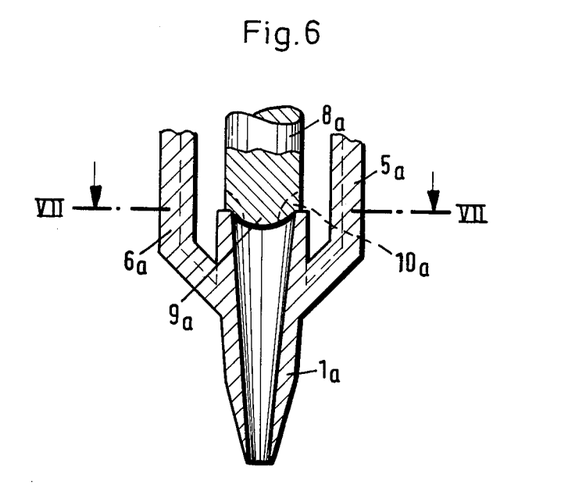
FIG. 6 is a part-sectional view similar to FIGS. 2 and 4 with an inserted closure pin which in this embodiment has a part-spherically shaped centering projection, however.
Figure 7:
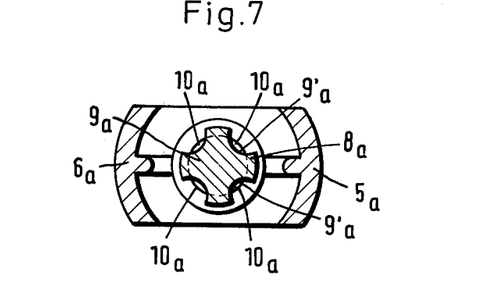
FIG. 7 is a sectional view taken aong line VII—VII of FIG. 6.

The centering projection may also be formed otherwise, for instance part-spherically as illustrated in FIGS. 6 and 7. There otherwise the same reference numerals have been used as in FIGS. 1 to 5, but with the addition of an appendix "a".

In order to provide for air exit apertures 10a, there are there provided four circumferentially spaced depressions 9a' in the sphere.

Figures 8, 9, 12:
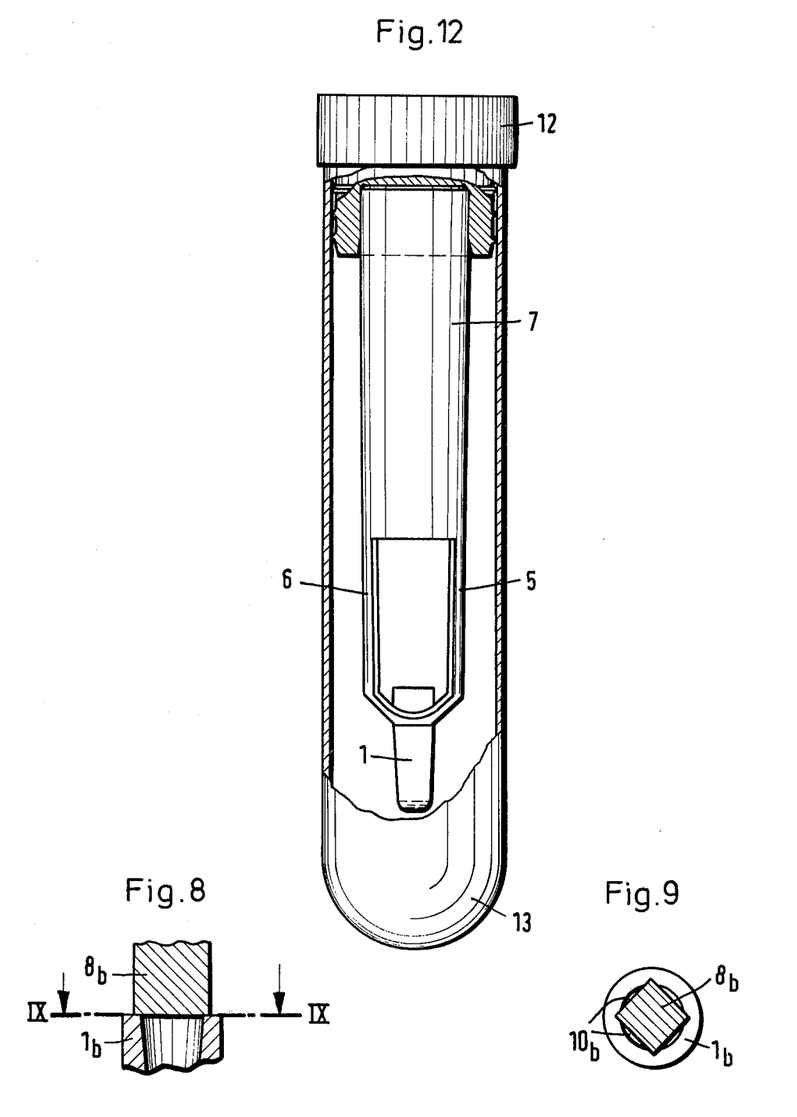
FIG. 8 is a part-sectional view of the rear end of the capillary with the applied closure pin having no centering projection.
FIG. 9 is a sectional view taken along line IX—IX of FIG. 8.
FIG. 12 is a partially cut-away side elevational view of a sample tube closed by plugs with a holder with a capillary inserted in the plug.

Finally, a centering projection may be dispensed with altogether and a closure pin 8b may be used having a planar face as illustrated in FIGS. 8 and 9. There the same reference numerals have again been used, but with the addition of a suffix "b". The size of the square face of the closure pin 8b is formed in such a way that this closure pin rests only with its four corners on the upper edges of the capillary 1b, but leaves free air exit apertures 10b therebetween.

Figure 10:
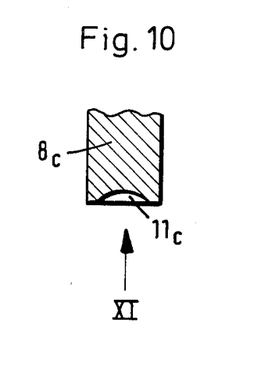
FIG. 10 is a partial view of the lower or front end of a closure pin with a depression.
Figure 11:
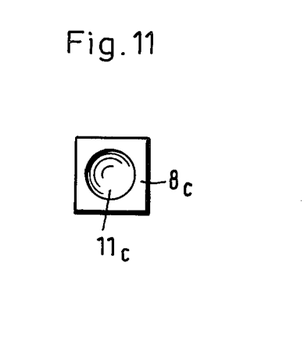
FIG. 11 is a view in direction of the arrow XI in FIG. 10.

In certain instances, it is of an advantage to provide a recess in the face of the closure pin, which recess then is able to receive the protruding lobe upon drawing in blood, said lobe resulting with no closure pin being provided. Such a configuration of the lower end of the closure pin is illustrated in FIGS. 10 and 11. The closure pin has there been denominated 8c and possesses a part-spherical recess 11c in its otherwise planar face. Since this pin also rests in the same fashion on the upper rim of the capillary 1 as the closure pin illustrated in FIGS. 8 and 9 does, there also air exit apertures are formed which do not obstruct the filling of the capillary with the blood drawn. The recess 11c is readily filled completely with blood. Thus, again an exact and constant dosage is effected.

The holder 4 or its upper tube 7 may be formed in the diameter in such a way that the tube 7 may be inserted clampingly at the top side into the void of a plug 12 associated to the device, as illustrated in FIG. 12. This plug may then be the closure plug of a sample tube 13 which serves to receive the device after extracted blood sample. The sample tube 13 is then filled in its lower part with water or some other liquid which is suited for a dilution of the blood sample. The closure pin with the retaining rod is of course pulled out prior to inserting the upper end of the tube 7 in the void of the plug 12 and discarded. Then by a slight tumbling movement the blood quantity in the capillary 1 may be flushed out with no difficulties and with no losses and mixed with the surrounding dilution liquid.

In order to avoid or keep negligibly low dosage errors thereby also, the lower end of the capillary 1 is formed as thin-walled as possible. This is done conveniently in that this lower end externally is provided with a steeper taper than the rest of the capillary. Should then as a result of a too deep immersion of the lower end 2 of the capillary 1 in the blood drop at the point of extraction nevertheless a wetting of the external taper be caused which could result in dosage errors, this external tapered surface may readily be wiped clean.

Figure 13:
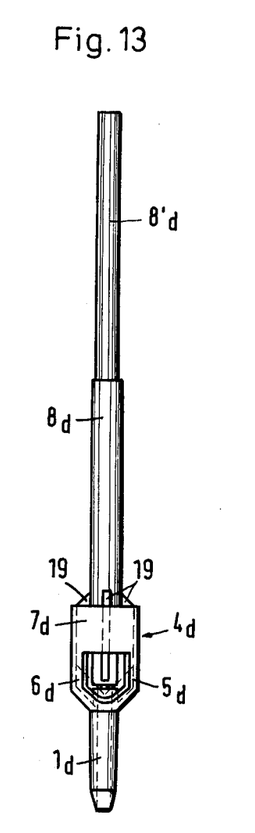
FIG. 13 is a side elevational view of a further embodiment of the capillary with holder and closure pin.
Figure 14:
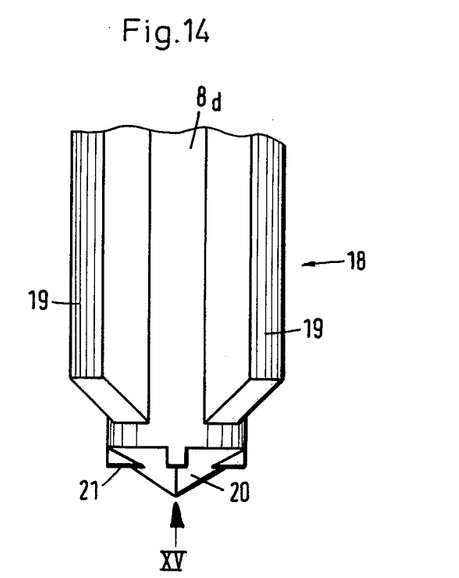
FIG. 14 is a partial view in an enlarged scale of the lower portion of the closure pin provided with guide vanes.
Figure 15:
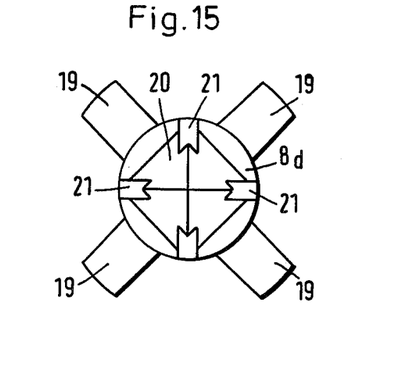
FIG. 15 is a view from the bottom of the lower portion of the closure pin as viewed in direction of the arrow XV in FIG. 14.

In the embodiment illustrated in FIGS. 13 to 15, the holder 4d for the capillary 1d is only relatively short; it in this instance also consists of an upper annular portion 7d and two webs 5d, 6d merging therefrom which carry the capillary 1d.

The closure pin 8d is offset at its rear end 8d' formed as a handle and possesses at is front end a pyramidal centering projection 20 which upon pushing in the holder finally emerges with its tip in the rear opening of the capillary. The four abutment surfaces 21 projecting from the roof edges of the pyramid which are best illustrated in FIGS. 14 and 15 engage the rear face of the capillary and thus keep the centering projection 20 in a predetermined distance from the rear capillary end.

The guide vanes 19 projecting from the lower end of the closure pin 8d radially outwardly fit tightly into the annular upper portion 7d of the holder 4d, but on the other hand permit a relative axial movement between the two.

In the embodiments according to FIGS. 16 to 18b a transverse wall is provided at the rear end of the capillary instead of a closure pin. The capillary 31 illustrated in FIG. 16, which is integrally connected to the two webs 35 and 36 and is made of transparent plastic possesses a slightly tapered, almost cylindrical bore 33 the inner width of which is only so large at the front end 32 that there the blood is reliably still sucked in by a capillary action.

Figure 16:
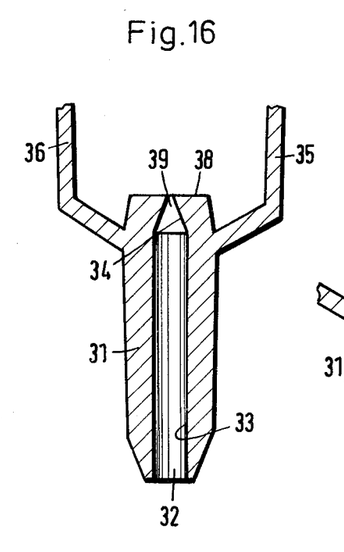
FIG. 16 is a part-sectional view of a further embodiment of the capillary with holder.

The bore 33 converges slightly in direction to the rear end which is constricted funnel-shaped at 34 and finally merges into a very narrow air exit aperture 39 which is located in the closure plane 38 of the rear transverse wall.

Figures 16A, 16B:
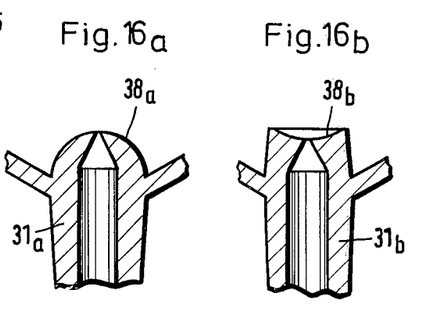
FIGS. 16a and 16b are partial views of a modified embodiment of the rear transverse wall of the capillary.

The capillary 31a illustrated in FIG. 16a possesses a rear transverse wall the closure surface 38a of which is semi-spherical so that the transverse wall is formed generally convex.

On the other hand, the capillary 31b illustrated in FIG. 16b possesses a slightly concave rear transverse wall the confining surface 38b of which is thus likewise depressed concavely.

Figure 17:
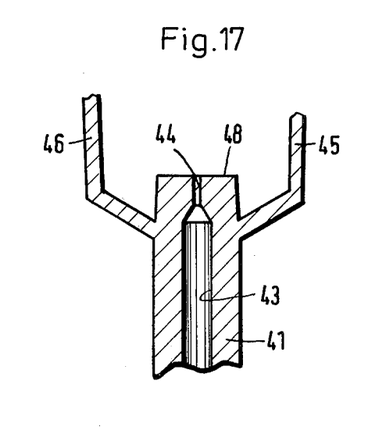
FIG. 17 is a part-sectional view of an embodiment similar to FIG. 16 with a different air exit aperture.

The capillary 41 illustrated in FIG. 17 likewise possesses an almost cylindrical bore 43 which is constricted likewise funnel-shaped at its rear end, but there merges into a small duct 44 which opens into the planar closure surface 48 of the rear transverse wall and serves as an air exit aperture.

The capillary 41 is supported by the two webs 45 and 46 of the holder.

Figure 17A:
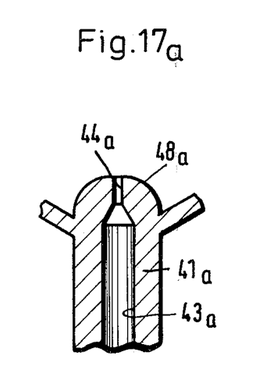
FIG. 17a is a modified embodiment of the rear transverse wall.

The capillary 41a illustrated in FIG. 17a possesses, similar to the embodiment of FIG. 16a, a rounded, generally semi-spherical closure surface 48a. The bore 43 of the capillary merges via a funnel-shaped constriction into a thin-duct-shaped air exit aperture 44a.

Figure 18:
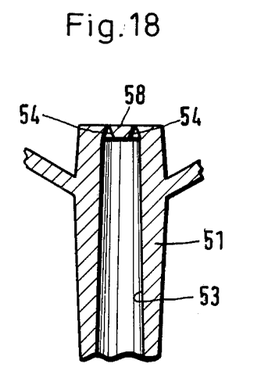
FIGS. 18 and 18a are partial views of further embodiments of the capillary with a transverse wall.
Figure 18A:
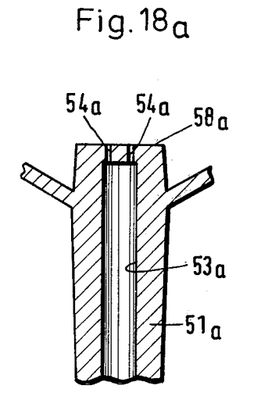

FIG. 18 shows a capillary 51 with a greater tapered bore 53 and a planar transverse wall having a planar closure surface 58 in which two funnel-shaped air exit apertures 54 open similar to the exit aperture 34 of FIG. 16.

In the modified embodiment of FIG. 18a and 18b, again small duct-shaped air exit apertures 54a are provided, similar to FIG. 17, which open into the closure plane 58a. Here also the bore 53a of the capillary 51a is formed conically constricted from the front to the rear.

Figure 18B:
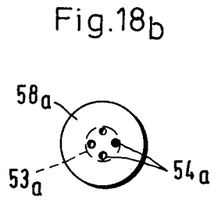

As will be noted from the plan view of the rear closure wall of FIG. 18b, a total of four air exit apertures 54a are provided which expel the air displaced by the blood entering from the bore 53a of the capillary.

What is claimed is:

1. A device for the extraction of capillary blood comprising:
   a capillary portion having front and rear ends;
   a capillary passage extending between said front and rear ends;
   a first opening a said front ends for the introduction of blood into said capillary passage by capillary action;
   a second opening at said rear end for venting said capillary passage;
   a holder at said rear end for supporting said capillary portion and having an outer surface;
   a closure pin axially movable within said holder between a first position in which said pin restricts the size of said second opening and a second position in which said pin does not restrict the size of said second opening; and
   window means in said holder communicating between said second opening and said outer surface.

2. A device as set forth in claim 1, wherein said capillary passage flares from said front end to said rear end.

3. A device for the extraction of capillary blood comprising:
- a capillary portion having front and rear ends;
- a capillary passage extending between said front and rear ends;
- an opening at said front end for the introduction of blood by capillary action into said capillary passage;
- a holder at said rear end for supporting said capillary portion and having an outer surface;
- a closure pin having an end face;
- an opening into said capillary passage at said rear end wherein said closure pin face and said rear end opening cooperate to define an air exit aperture smaller in area than said capillary passage;
- window means in said holder communicating between said air exit aperture and said outer surface; and
- a guide and retaining rod integrally connected with said closure pin, said guide and retaining rod being displacable in an axial direction relative to said holder.

4. A device as set forth in claim 3, further comprising: means for clampingly locating said rod in said holder with said closure pin end face contacting said capillary portion rear end at said rear end opening.

5. A device as set forth in claim 4, wherein said retaining rod for said closure pin is formed as an extended handle.

6. A device as set forth in claim 4, wherein said means for clampingly locating said rod in said holder comprises at least three guide vanes projecting radially from the axis of said rod.

7. A device as set forth in claim 3, wherein closure pin has a centering projection at said end face.

8. A device as set forth in claim 7, wherein said centering projection is part-spherical.

9. A device as set forth in claim 8, wherein said part spherical centering projection has a periphery including recesses formed therein, said recesses cooperating with said rear end opening to define said air exit apertures.

10. A device as set forth in claim 7, wherein said centering projection is of pyramidal form defining a number of roof edges.

11. A device as set forth in claim 10, wherein said roof edges include abutment noses having abutment surfaces, said abutment surfaces radially projecting from said closure pin.

12. A device as set forth in claim 3, wherein said closure pin has a depression in said end face.

* * * * *